United States Patent
Weiss et al.

(10) Patent No.: US 9,610,109 B2
(45) Date of Patent: Apr. 4, 2017

(54) WEDGE SHAPED FRACTURE FIXATION DEVICES AND METHODS FOR USING THE SAME

(75) Inventors: Arnold-Peter C. Weiss, Barrington, RI (US); Amy L. Ladd, Standford, CA (US); Roy Fiebiger, Los Gatos, CA (US); Gary B. Hulme, San Jose, CA (US); Jeffrey J. Christian, Morgan Hill, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/585,448

(22) Filed: Aug. 14, 2012

(65) Prior Publication Data

US 2013/0211522 A1  Aug. 15, 2013

Related U.S. Application Data

(60) Provisional application No. 61/524,232, filed on Aug. 16, 2011.

(51) Int. Cl.
*A61B 17/86* (2006.01)
*A61F 2/28* (2006.01)
(Continued)

(52) U.S. Cl.
CPC ............ *A61B 17/863* (2013.01); *A61B 17/68* (2013.01); *A61B 17/8625* (2013.01);
(Continued)

(58) Field of Classification Search
CPC .............. A61B 17/7098; A61B 17/809; A61B 17/8095; A61B 17/863; A61B 17/8645;
(Continued)

(56) References Cited

U.S. PATENT DOCUMENTS 3,939,828 A  2/1976  Mohr et al.
4,450,591 A  5/1984  Rappaport
(Continued)

FOREIGN PATENT DOCUMENTS

DE  4109941  10/1992
EP  1772108   4/2007
(Continued)

OTHER PUBLICATIONS

International Search Report dated Jan. 13, 2013, issued in corresponding International Application No. PCT/US2012/050769.
(Continued)

*Primary Examiner* — Matthew Lawson
*Assistant Examiner* — Amy Sipp
(74) *Attorney, Agent, or Firm* — Lerner, David, Littenberg, Krumholz & Mentlik, LLP

(57) ABSTRACT

Reduced bone fracture fixation devices and methods for using the same are provided. Aspects of the reduced bone fracture fixation devices include a body dimensioned to be positioned in a reduced bone fracture, wherein the body has a wedge shape configuration sufficient to exert a force on bone of the reduced bone fracture and maintain reduction of the reduced bone fracture. The devices, kits and methods of the invention find use in a variety of applications, such as in applications in which it is desired to repair a reduced bone fracture.

20 Claims, 10 Drawing Sheets

(51) Int. Cl.
*A61B 17/68* (2006.01)
*A61B 17/88* (2006.01)
*A61B 17/80* (2006.01)

(52) U.S. Cl.
CPC ............ *A61B 17/8802* (2013.01); *A61F 2/28* (2013.01); *A61F 2/2846* (2013.01); *A61B 17/8095* (2013.01); *A61B 17/864* (2013.01)

(58) Field of Classification Search
CPC .......... A61B 2017/681; A61B 17/8635; A61B 17/864; A61F 2/44; A61F 2/4455; A61F 2002/4475; A61F 2002/30112; A61F 2002/3015
USPC ....... 606/300, 301, 304, 309, 314, 316, 317, 606/321, 323; 623/17.16
See application file for complete search history.

(56) References Cited

U.S. PATENT DOCUMENTS

| | | | |
|---|---|---|---|
| D274,359 S | 6/1984 | Christensen et al. | |
| 4,834,757 A * | 5/1989 | Brantigan | 623/17.11 |
| 5,360,450 A | 11/1994 | Giannini | |
| 5,387,241 A | 2/1995 | Hayes | |
| 5,456,685 A | 10/1995 | Huebner | |
| 5,458,642 A | 10/1995 | Beer et al. | |
| 5,470,334 A * | 11/1995 | Ross | A61B 17/8615 606/104 |
| 5,562,672 A | 10/1996 | Huebner et al. | |
| 5,609,636 A * | 3/1997 | Kohrs | A61F 2/4455 606/247 |
| 5,676,702 A | 10/1997 | Ratron | |
| 5,683,463 A * | 11/1997 | Godefroy | A61F 2/446 623/17.16 |
| 5,741,259 A | 4/1998 | Chan | |
| 5,749,875 A | 5/1998 | Puddu | |
| 5,758,420 A | 6/1998 | Schmidt et al. | |
| 5,766,251 A | 6/1998 | Koshino | |
| 6,008,433 A | 12/1999 | Stone | |
| 6,030,162 A * | 2/2000 | Huebner | A61B 17/1682 411/263 |
| 6,045,554 A | 4/2000 | Grooms et al. | |
| 6,086,593 A | 7/2000 | Bonutti | |
| 6,096,060 A * | 8/2000 | Fitts | A61B 17/0401 606/232 |
| 6,129,730 A * | 10/2000 | Bono | A61B 17/8047 606/271 |
| 6,136,032 A | 10/2000 | Viladot Perice et al. | |
| 6,168,631 B1 | 1/2001 | Maxwell et al. | |
| 6,190,414 B1 | 2/2001 | Young et al. | |
| 6,302,914 B1 * | 10/2001 | Michelson | 623/17.16 |
| 6,375,655 B1 * | 4/2002 | Zdeblick et al. | 623/17.16 |
| 6,554,835 B1 | 4/2003 | Lee | |
| 6,554,862 B2 | 4/2003 | Hays et al. | |
| 6,572,653 B1 | 6/2003 | Simonson | |
| 6,629,977 B1 | 10/2003 | Wolf | |
| 6,666,888 B1 * | 12/2003 | Jackson | A61F 2/446 623/17.11 |
| 6,743,257 B2 | 6/2004 | Castro | |
| 6,823,871 B2 | 11/2004 | Schmieding | |
| 6,875,216 B2 | 4/2005 | Wolf | |
| 7,001,385 B2 | 2/2006 | Bonutti | |
| 7,033,398 B2 | 4/2006 | Graham | |
| 7,101,400 B2 | 9/2006 | Thramann | |
| 7,201,776 B2 | 4/2007 | Ferree et al. | |
| 7,322,986 B2 | 1/2008 | Wolf | |
| 7,678,153 B2 | 3/2010 | Katz et al. | |
| 7,695,471 B2 | 4/2010 | Cheung et al. | |
| D620,112 S * | 7/2010 | Courtney et al. | D24/155 |
| 7,811,286 B2 | 10/2010 | Medoff | |
| 7,867,252 B2 * | 1/2011 | Criscuolo et al. | 606/232 |
| 7,867,276 B2 | 1/2011 | Matge et al. | |
| 7,922,730 B2 | 4/2011 | Raines, Jr. | |
| 8,092,547 B2 | 1/2012 | Lepow et al. | |
| 8,182,489 B2 * | 5/2012 | Horacek | 606/87 |
| 8,226,714 B2 * | 7/2012 | Beck et al. | 623/13.12 |
| 8,545,572 B2 | 10/2013 | Olson | |
| 8,628,582 B2 | 1/2014 | Lavi | |
| 8,906,097 B2 * | 12/2014 | Mather et al. | 623/17.16 |
| 8,979,874 B2 * | 3/2015 | Darois et al. | 606/151 |
| 2002/0038123 A1 | 3/2002 | Visotsky et al. | |
| 2002/0087161 A1 * | 7/2002 | Randall et al. | 606/73 |
| 2002/0138147 A1 * | 9/2002 | Cohen | 623/17.16 |
| 2002/0183846 A1 * | 12/2002 | Kuslich et al. | 623/17.11 |
| 2003/0065393 A1 * | 4/2003 | Moumene et al. | 623/17.11 |
| 2003/0125744 A1 * | 7/2003 | Contiliano | A61B 17/864 606/916 |
| 2004/0172031 A1 * | 9/2004 | Rubecamp | A61B 17/8685 606/309 |
| 2005/0101961 A1 * | 5/2005 | Huebner et al. | 606/72 |
| 2005/0125063 A1 | 6/2005 | Matge et al. | |
| 2005/0177165 A1 * | 8/2005 | Zang et al. | 606/73 |
| 2005/0187636 A1 * | 8/2005 | Graham | A61B 17/562 623/21.18 |
| 2006/0041315 A1 * | 2/2006 | Katz et al. | 623/21.11 |
| 2006/0085067 A1 * | 4/2006 | Gradel | A61F 2/446 623/17.11 |
| 2006/0155286 A1 * | 7/2006 | Wang | 606/73 |
| 2006/0189992 A1 | 8/2006 | Medoff | |
| 2006/0190088 A1 * | 8/2006 | Parks | A61B 17/562 623/21.11 |
| 2006/0229622 A1 * | 10/2006 | Huebner et al. | 606/73 |
| 2007/0010848 A1 | 1/2007 | Leung et al. | |
| 2007/0156147 A1 | 7/2007 | Wang et al. | |
| 2007/0173954 A1 * | 7/2007 | Lavi | A61B 17/562 623/21.11 |
| 2007/0198018 A1 * | 8/2007 | Biedermann et al. | 606/73 |
| 2008/0154381 A1 | 6/2008 | Parrish | |
| 2008/0161864 A1 * | 7/2008 | Beck et al. | 606/326 |
| 2008/0208349 A1 | 8/2008 | Graser | |
| 2008/0293014 A1 * | 11/2008 | Chung | 433/174 |
| 2009/0024174 A1 * | 1/2009 | Stark | A61B 17/8625 606/321 |
| 2009/0043308 A1 * | 2/2009 | Horacek | 606/87 |
| 2009/0099664 A1 | 4/2009 | Forrester | |
| 2009/0125071 A1 * | 5/2009 | Skinlo et al. | 606/300 |
| 2009/0182336 A1 | 7/2009 | Brenzel et al. | |
| 2009/0204214 A1 * | 8/2009 | Fuji et al. | 623/17.11 |
| 2009/0254129 A1 * | 10/2009 | Tipirneni et al. | 606/309 |
| 2009/0276046 A1 * | 11/2009 | Parks et al. | 623/16.11 |
| 2010/0030135 A1 * | 2/2010 | Mitchell | 604/48 |
| 2010/0042215 A1 * | 2/2010 | Stalcup et al. | 623/16.11 |
| 2010/0217391 A1 | 8/2010 | Ladd | |
| 2010/0240010 A1 * | 9/2010 | Holmstrom | 433/174 |
| 2010/0280625 A1 | 11/2010 | Sanders et al. | |
| 2010/0318088 A1 * | 12/2010 | Warne | A61B 17/15 606/87 |
| 2011/0060373 A1 * | 3/2011 | Russell et al. | 606/304 |
| 2011/0071579 A1 | 3/2011 | Reach, Jr. | |
| 2011/0092992 A1 * | 4/2011 | Darois | A61B 17/064 606/151 |
| 2012/0156647 A1 * | 6/2012 | Yoon et al. | 433/174 |
| 2012/0191208 A1 * | 7/2012 | Olson | 623/21.18 |
| 2012/0237898 A1 * | 9/2012 | Palti et al. | 433/174 |
| 2012/0264086 A1 * | 10/2012 | Hansson et al. | 433/174 |
| 2013/0013003 A1 * | 1/2013 | Carbone et al. | 606/305 |
| 2013/0273499 A1 * | 10/2013 | Hansson et al. | 433/174 |
| 2015/0051705 A1 * | 2/2015 | James et al. | 623/17.16 |

FOREIGN PATENT DOCUMENTS

| | | |
|---|---|---|
| FR | 2919488 | 2/2009 |
| WO | 9106261 | 5/1991 |
| WO | 2005120400 | 12/2005 |
| WO | 2006091807 | 8/2006 |
| WO | 2008125849 | 10/2008 |
| WO | 2009100200 | 8/2009 |
| WO | 2009125242 | 10/2009 |
| WO | 2009125243 | 10/2009 |
| WO | 2010096664 A1 | 8/2010 |

(56) References Cited

FOREIGN PATENT DOCUMENTS

OTHER PUBLICATIONS

International Search Report and Written Opinion dated Apr. 23, 2010, issued in corresponding International Application No. PCT/US2010/024753.
Newton, C. 'Principles and Techniques of Osteotomy' retrieved from Internet <URL: http:cal.vet.upenn.edu/projects/saortho/chapter_40/40mast.htm>, Textbook of Small Animal Orthopedics, 1985, Chapter 40.
M. Mofid, et al., "Spring-Mediated Mandiated Mandibular Distraction Osteogenesis," J. Craniofacial Surgery 14(5): 756-762 (2003).
"Arthrex Flatfoot Solutions", Copyright 2009, 2 pages.
"BIOARCH Subtalar Implant System: Surgical Technique", Copyright 2014, 4 pages.
"CSTS Conical Subtalar Spacer: Minimally Invasive Answer for Flexible Flatfoot OrthoPro CSTS", CSTS Brochure, Prior Art Publicly available prior to Aug. 16, 2011, 2 pages.
"Subfix Arthoeresis Implant: Foot and Ankle Surgery", SBF40000-A-060810, 2010, 4 pages.
ACUMED, "BIOTRAK Headless Resorbable Compression Screw", 2009, 12 pages.
Bach, Bernard R. Jr., "Observations on Interference Screw Morphologies", Special Report, The Journal of Arthroscopic and Related Surgery, vol. 16, No. 5, (Jul.-Aug. 2000): E10, 6 pages.
INSTRATEK, "Sub-Talar Lok: Arthroereisis Implant System", Prior Art Publicly available prior to Aug. 16, 2011, 2 pages.
Integra, "Subtalar MBA and bioBLOCK Implant: Surgical Technique", Copyright 2011, 12 pages.
Tornier, "Futura Conical Subtalar Implant", <www.tornier-us.com_lower_ankle_ankrec002>, Printed: Jan. 14, 2016, 2 pages.
Vilex Restoring Mobility, "Talus of Vilex—TOV: Correction of Flatfoot in Children and Adults", Copyright 2008, 2 pages.

* cited by examiner

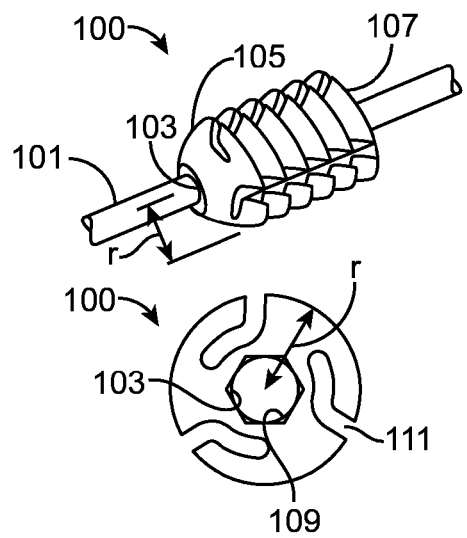
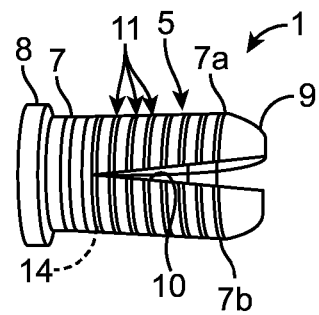
FIG. 5I      FIG. 5J
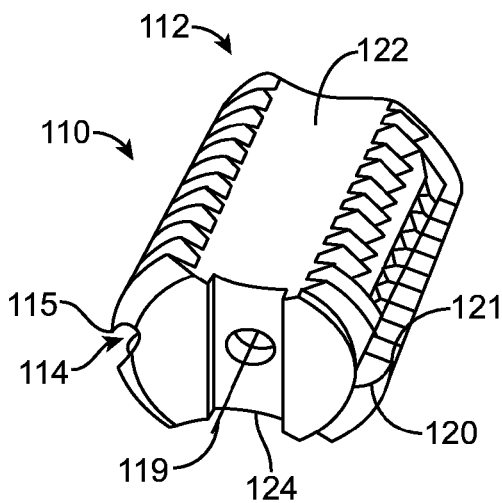
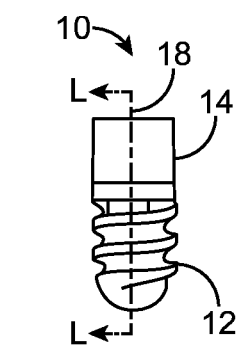
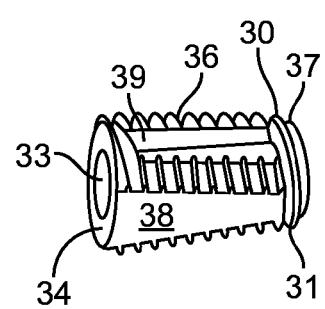
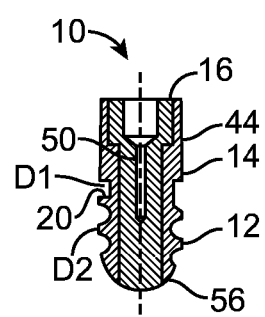
FIG. 5K      FIG. 5L

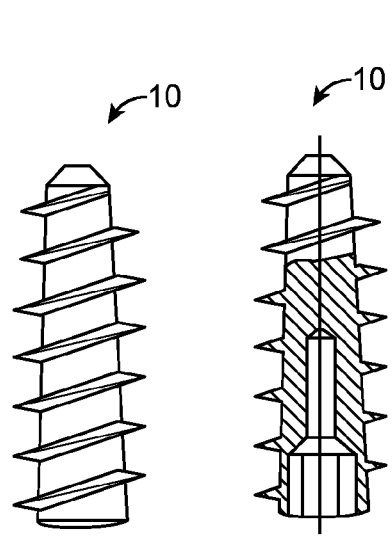
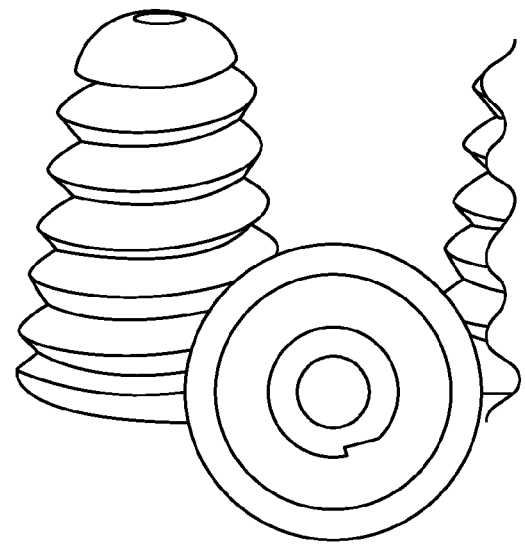
FIG. 5M     FIG. 5N
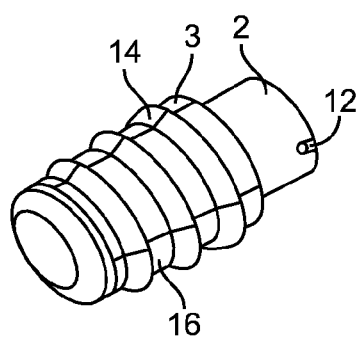
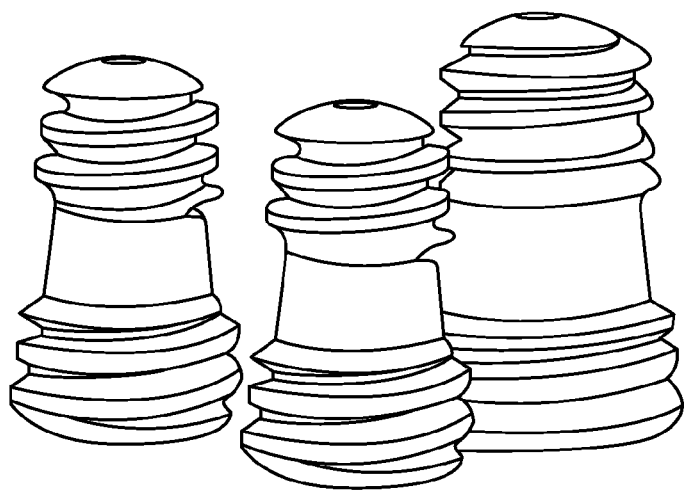
FIG. 5O     FIG. 5P

WEDGE SHAPED FRACTURE FIXATION DEVICES AND METHODS FOR USING THE SAME

CROSS-REFERENCE TO RELATED APPLICATIONS

Pursuant to 35 U.S.C. §119 (e), this application claims priority to the filing date of U.S. Provisional Patent Application Ser. No. 61/524,232, filed Aug. 16, 2011, which application is incorporated herein by reference in its entirety.

INTRODUCTION

Bone or fracture voids may occur in many different types of bones in many different ways. For example, an unstable distal radius fracture is common especially in the endemic osteoporotic populations of North America, Europe, Asia, and Australia. This type of low energy fracture may be sustained by a fall on an outstretched hand. The classic, osteopenic osteoporotic fragility fracture is extra-articular or includes a simple intra-articular component, i.e., the fracture is primarily outside of a joint or may include a simple component within the joint. The fracture may result in dorsal comminution, loss of radial height, loss of volar tilt, radial shift, and shortening. In this regard, dorsal comminution refers to pulverization of the bone in the wrist in the direction of the back of the hand, loss of radial height refers to loss of height in the wrist on the side near the thumb, loss of volar tilt refers to loss of tilt in the wrist in the direction of the palm of the hand, and radial shift refers to shift of the wrist towards the side of the thumb. In addition, poor bone mineral quality and the degree of comminution, especially with proximal extension on the radial column, may render this fracture unstable, such that closed treatment alone may be insufficient. Further, the forces experienced by the wrist during daily activities are primarily compression, e.g., digital motion, and shear/torsion, e.g., forearm rotation. Fracture, e.g., catastrophic collapse, occurs typically in tension, thereby creating a relatively transverse fracture across the metaphysis, the metaphysis being the part of a bone between the shaft of the bone, i.e. diaphysis, and the end of the bone, i.e., epiphysis. The position of the wrist, the forces applied, and the bone quality may determine other components of the fracture, such as, for example, extension into the joint, extension into the diaphysis, and more oblique components from torsional forces.

Reduction, i.e., architectural restoration, of a simple but unstable fracture may be obtained through a variety of means. Although there has been a historical preference for non-operative treatment, more invasive treatments intended to restore cortical, i.e. external or surface, integrity have historically included pins and plaster techniques, external fixation, and cross metaphyseal pinning. Later treatment techniques have included dorsal plating systems that address the radial column, and volar plate fixation. Examples of dorsal plating systems include, e.g., Forte Zimmer low profile plate or Synthes pi plate. The more rigid construct required for volar fixation, given its application on the compression side of the radius, has been purportedly outweighed by soft tissue coverage of the volar plate not afforded by dorsal plating systems.

Although plating systems may address cortical reconstitution, they do not address metaphyseal bone voids that are formed when osteopenic/osteoporotic bone collapses. Further, rigid volar plates may not adequately overcome the loss of cancellous bone in the metaphysis when significant comminution and severe loss of bony architecture has occurred. To fill these metaphyseal voids, autograft bone, banked allograft bone, and/or synthetic fillers, e.g., calcium phosphate or calcium sulfate, may be used. Moreover, although PMMA (polymethyl-methacrylate) cement has historically been used as a void filler, this material is rarely used in radius fractures since biologic and biologically active alternatives are preferred.

Plating systems and volar plate fixation may be more substantial and invasive than a patient's bone or fracture void and co-morbidities may warrant. While such fractures may frequently be reduced (architectural reconstitution) by closed manipulation and successfully casted, follow-up examination in the casting period over the next few weeks often shows that fragility fractures experience loss of reduction with resulting deformity. The typical patient with a fragility fracture is elderly and has co-morbid health conditions, which underscores the importance of minimizing risk at the same time as improving treatment methods. In these patients, it is the maintenance of the fracture reduction that is the challenge rather than obtaining a satisfactory reduction in the first place. Aggressive open fracture treatment is best avoided if it is not necessary to obtain reduction.

SUMMARY

Reduced bone fracture fixation devices and methods for using the same are provided. Aspects of the reduced bone fracture fixation devices include a body dimensioned to be positioned in a reduced bone fracture, wherein the body has a wedge shaped configuration to exert a force on bone of the reduced bone fracture sufficient to maintain reduction of the reduced bone fracture. Aspects of the invention further include kits and methods of using and manufacturing the bone fracture fixation devices. The devices, kits and methods of the invention find use in a variety of applications, such as in applications in which it is desired to repair a reduced bone fracture.

DETAILED DESCRIPTION

Figure 2:
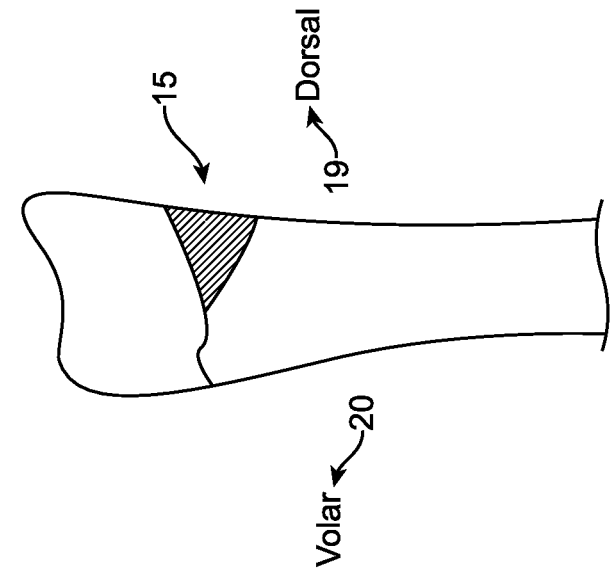
FIG. 2 is a schematic side view of a distal radial bone fracture.

Reduced bone fracture fixation devices and methods for using the same are provided. Aspects of the reduced bone fracture fixation devices include a body dimensioned to be positioned in a reduced bone fracture, wherein the body has a wedge shape configured to exert a force on bone of the reduced bone fracture sufficient to maintain reduction of the reduced bone fracture. Aspects of the invention further include kits and methods of using and manufacturing the bone fracture fixation devices. The devices, kits and methods of the invention find use in a variety of applications, such as in applications in which it is desired to repair a reduced bone fracture.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention in greater detail, embodiments of devices of the invention are reviewed first, followed by descriptions of embodiments of the methods and manufacture and use of the devices, as well as kits that include the devices.

Devices

Reduced bone fracture fixation devices according to embodiments of the invention are devices that are configured to maintain reduction of a reduced bone fracture. In some instances, the devices can be used to reduce a bone fracture. By "reduced bone fracture" is meant a bone fracture wherein the fractured pieces of bone have been restored to their normal or nearly normal anatomic alignment. The goal of fracture treatment is to maintain the bone in a reduced position, i.e., properly aligned, while the bone heals. Accordingly, a reduced bone fracture is a fracture in which the fractured pieces of bone have been restored to the substantially normal, if not normal, anatomic alignment. As is known in the art, a fracture may be reduced by a variety of different reduction protocols. Reduced bone fractures with which devices of the invention find use are fractures that have been reduced using any convenient protocol.

As indicated above, the subject devices are configured to exert a force on one or more bone surfaces of a reduced bone fracture to maintain the bone in a reduced (i.e., anatomically or nearly anatomically aligned) position. The subject devices can exert forces that include but are not limited to: distraction forces (i.e., forces in which pieces of bone are forced in opposite directions), torsional forces (to prevent a piece of fractured bone from rotating), expansion forces (to resist compression), retention forces (to prevent a bone fragment from migrating), etc.

The reduced bone fracture fixation devices of the subject invention have a body dimensioned to be positioned in a reduced bone fracture. By "dimensioned to be positioned in a reduced bone fracture" is meant that the body of the device can be any size suitable for positioning in the reduced fracture site of interest, which can include, but is not limited to, the distal radius, proximal humerus, proximal tibia, calcaneus, vertebral body, hip, etc. In some embodiments, devices in accordance with the invention are configured to fit entirely within a reduced bone fracture void, such that no portion of the device extends outside of or along an outer surface of the bone. The dimensions of the subject devices can vary according to the size of the bone at the reduced fracture site of interest, the extent or size of the fracture, the size of the subject (e.g., child or adult), etc. The subject devices can be positioned so that they are located entirely within the fracture site; i.e., no portion of the device extends outside of the bone, which minimizes irritation of the surrounding soft tissues. In certain embodiments, the devices have a longest dimension ranging from 3 mm to 6 cm, such as 4 mm to 5 cm, including 8 mm to 4 cm.

In some embodiments, devices of the invention are configured to function as a cavity-filling wedge. Devices of these embodiments are referred to herein as wedge implant devices and have a wedge-shaped configuration. In these embodiments the devices are configured to maintain separation, in other words to sustain a separating force, on two or more bone surfaces such that the device maintains reduction of a reduced fracture. In some instances, the device is constructed of a hard (i.e., non-compliant) material (e.g., stainless steel, titanium, or other porous on non-porous metal, or a non-metallic, specialized medical grade polymer such as polyetheretherketone-PEEK, etc.) configured to conform to a fracture site of interest (e.g., a conical screw). In some instances, the device is constructed of autograft or allograft bone. Devices of interest can include a body dimensioned to be positioned in the reduced bone fracture, such that the device can exert a force on bone of the reduced bone fracture sufficient to maintain reduction of the reduced bone fracture. In some embodiments, one end of the device has a cross-sectional area that is greater in size than the other end (e.g., as found in shapes such as conical shapes, trapezoid shapes, pyramidal shapes, etc.). In some instances the proximal and distal ends of the device can be approximately the same size (e.g., a cylinder, a triangular prism). The device can also be any three-dimensional geometric shape configured to conform to a fracture site of interest (e.g., tetrahedron, pentagonal prism, etc.). When deployed, the subject devices can exert force on a single bone portion of the reduced bone fracture or two or more different bone portions, depending on a number of factors, such as the particular device configuration, the anatomical structure of the reduced fracture, etc.

The amount and direction of the force exerted by the reduced bone fracture fixation devices of the invention can be determined by a number of factors, including variations in the configuration of the device, differences in the material used to construct the subject devices, differences in the dimensions or thickness of the subject device, etc. In some instances, the force exerted can range, for example, from 5 to 250N, such as 7.5 to 200N, where certain ranges of interest include 8N to 26N, such as from 22N to 178N, or 44N to 89N.

The subject devices can have different configurations, which can vary depending on the materials and methods used for constructing the device. Configurations of the subject devices can include, but are not limited to: a trimodal configuration, a conical configuration, etc. In some instances, the devices can be formed by a combination of any of the above configurations. Embodiments of the subject devices with various configurations are discussed further below.

The subject devices may be fabricated using any convenient protocol. For example, the subject devices can be produced by molding, stamping, bending or machining, etc.

As mentioned above, devices of the invention are reduced fracture fixation devices. The devices may be configured for use with a wide variety of different types of reduced fractures. Different types of reduced fractures of interest include, but are not limited to: fractures of the radius, ulna, humerus, femur, tibia, fibula, clavicle, scapula, spine, vertebral body, ribs, pelvis, carpal bones, tarsal bones, metacarpals, metatarsals, etc., and the like.

Figure 1:
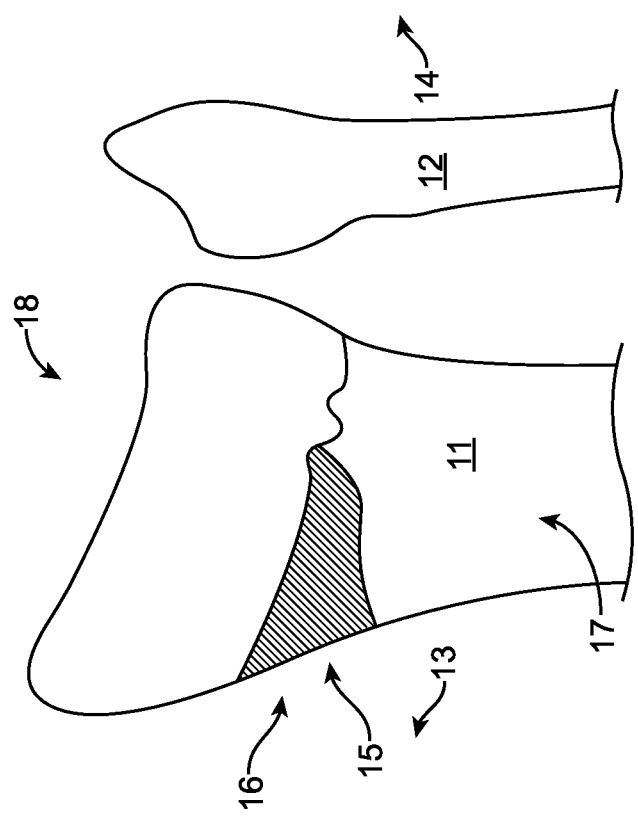
FIG. 1 is a schematic antero-posterior view of a distal radial bone fracture.

In some embodiments, the reduced fracture is a reduced distal radius fracture. FIG. 1 is a schematic anteroposterior view of a wrist, illustrating a distal radius fracture 15 in the radius 11. Also shown is ulna 12. The distal radial bone fracture 15 is situated on the radial side 13 of the radius 11 opposite the ulnar side 14. The distal radial bone fracture 15 is located in the metaphysis 16 of the radius 11, between the diaphysis 17 and the epiphysis 18 of the radius 11. The bone fracture 15 as shown has created a metaphyseal void (shaded) on the radial side 13 of the radius 11.

FIG. 2 illustrates a schematic side view of a distal radial bone fracture 15, viewed from the radial side of the wrist. FIG. 2 illustrates only the radius 11, since in this view the ulna 12 is substantially hidden behind the radius 11. The side view shows that the bone fracture 15 is located predominantly on the dorsal aspect 19 of the radius 11, opposite the volar side 20. The bone fracture as shown has created a metaphyseal void (shaded) on the dorsal aspect 19 of the radius 11.

The bone fracture 15 illustrated in FIGS. 1 and 2 is an example of an unstable, distal radius fracture that is extra-articular, i.e., the fracture is located outside of a joint. The fracture 15 as shown may result in dorsal comminution, i.e., pulverization of the bone on the dorsal side 19 of the radius 11. The fracture 15 as shown may also result in loss of radial height, i.e., loss of height of the bone on the radial side 13 of the radius. In addition, the fracture 15 as shown may result in loss of volar tilt, i.e., loss of tilt of the bone towards the volar side 20 of the radius 11. Further, the fracture 15 as shown may result in radial shift, i.e., shift of the bone towards the radial side 13 of the radius 11. Moreover, the fracture 15 as shown may result in shortening of the radial column.

Trimodal Embodiment

In one embodiment, the reduced bone fracture fixation device has a trimodal configuration, in that it has substantially three "faces," where any two of the faces are connected to the other by a rounded edge. The body of the device can taper from a wider diameter at the proximal end of the device to a narrow diameter (e.g., a point, such as element 31 in FIG. 3) at the distal end of the device. In some instances, the implant does not have a "head", that is, a component designed to engage with a screwdriver. The body of the trimodal embodiment can be solid or it can be at least partially hollow. As such, at least a portion of the interior volume of the implant may be void space. For example, the device can have an internal passageway through at least a portion of the length of the device, e.g., the distal end of the device.

In some instances in which the implant is hollow, the screw is cannulated (e.g., element 420 in FIG. 4), such that an internal passageway is defined inside of the implant from one end of the implant to the other, i.e., the implant is tubular. In a cannulated embodiment, the device can have an internal passageway extending the length of the device, e.g., from the proximal portion of the implant to the distal point of the implant.

Figure 3:
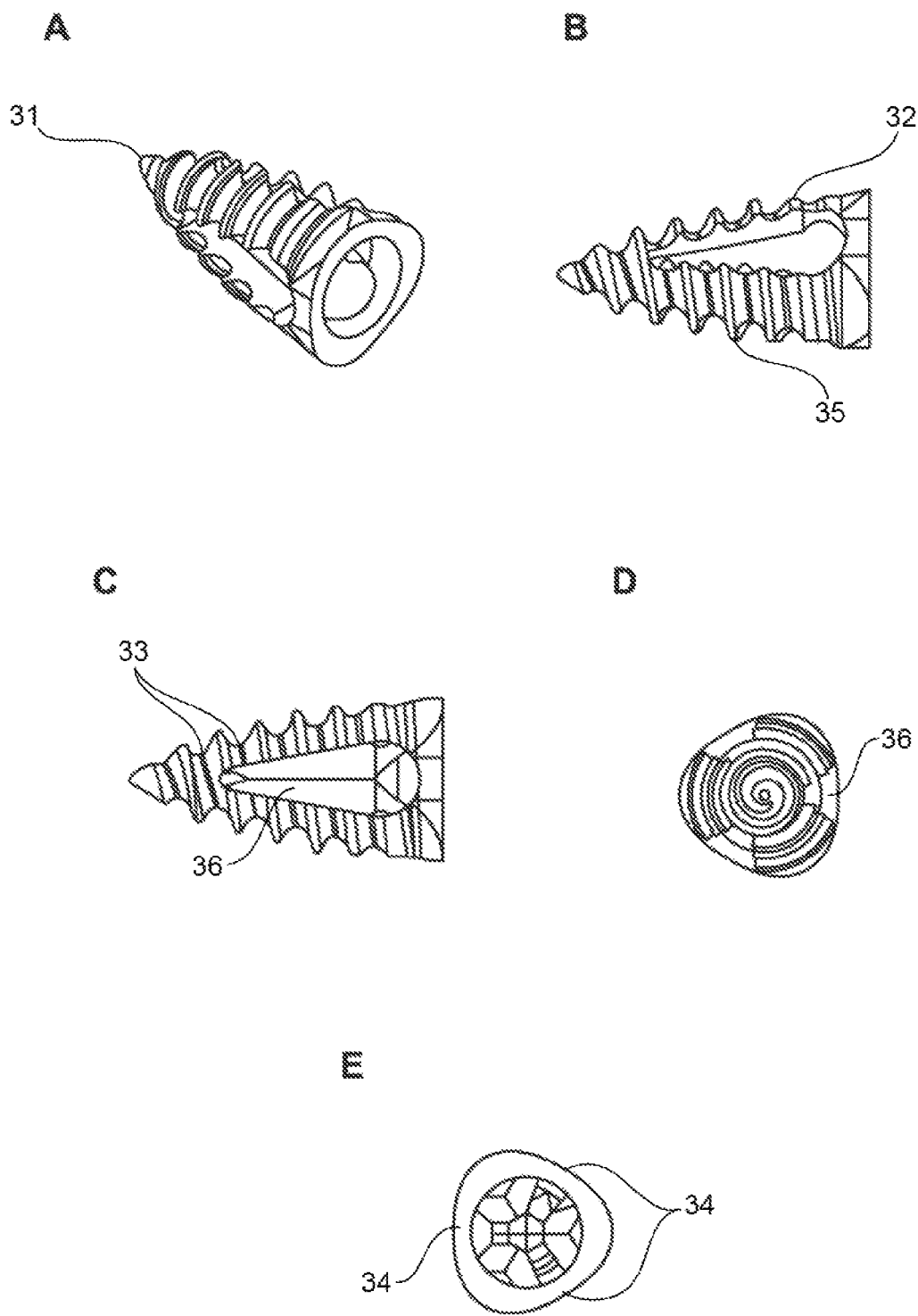
FIGS. 3A-E provide schematic perspective views of an embodiment of a reduced bone fracture fixation device.

As reviewed above, in these embodiments the reduced bone fracture fixation device has a trimodal configuration, where the device may further have one or more straight edges (such as two or more straight edges, including three or more straight edges, etc.) around the circumference of the device (e.g., element 34 in FIG. 3), or concave, convex, or angled surfaces, such as two or more, three or more, etc. The base or proximal end of the device can have a cross-sectional profile that may range from a circular shape to a triangular shape, including a triangle with rounded corners as shown in the end-view of the device in FIGS. 3D and E. For example, the device can be an implant comprising a distal point, as shown in FIG. 3, with a rounded triangle shape at the base. Further, the base can be configured to cooperate with one or more tools, such as a screwdriver to insert the device to a reduced bone fracture site of interest or with a grasping tool used to reposition or remove the device if necessary. In embodiments in which the device has an internal passageway or opening, the opening forms a "wall", i.e., the portion of the device that surrounds the opening. In some embodiments the wall of the device is continuous around the entire circumference of the device. In some embodiments, one or more portions of the wall can have cut-outs such that the wall has "windows", or openings, where there is communication between the internal passageway of device and the outside of the body of the device through the opening in the wall. In some instances the device may have one cut-out, or more than one cut-out, such as two, three, or more cut-outs. The wall cut-outs can be configured to allow bone growth through the opening (e.g., osteo-integration), which can aid in maintaining the device in the desired position in the bone. The cut-outs, when present, can be any suitable shape (e.g., oval, ellipse, rectangle, etc.) or size, and can have any orientation with respect to the long axis of the device (e.g. longitudinal, diagonal, transverse, etc.) See, for example, the cut-out shown as element 36 in FIG. 3C (side view of device) and FIG. 3D (end-view of the device).

The reduced bone fracture fixation devices can also include one or more bone securing elements. By "bone securing element" is meant an element configured to secure the reduced bone fracture fixation device to bone at the surface of a reduced bone fracture or fracture void, such that the position of the reduced bone fracture device is maintained once it has been placed into the reduced fracture site (in other words, the device retains its position following placement). The bone securing element can be, for example, one or more threads on the outside surface of the device, such as threads on a screw. For example, a device can have an external thread originating at the distal end of the screw. The bone securing element can also be barbs; hooks; loops; bumps; spurs; footholds; knuckles; coils, anchors; or other features etc.

Figure 4:
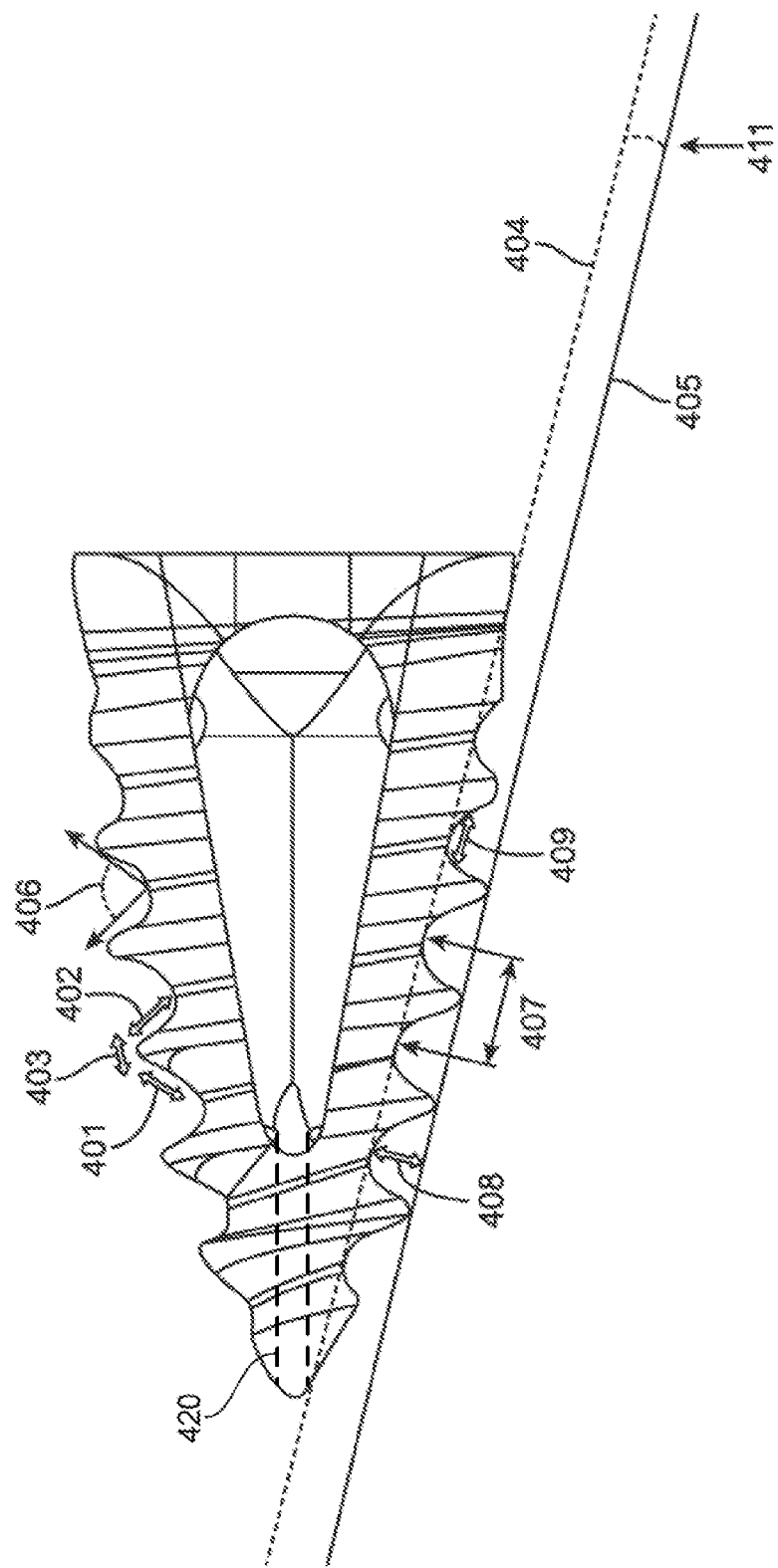
FIG. 4 is a magnified schematic perspective view of FIG. 3C.

In one embodiment of the device configuration as shown in FIGS. 3 and 4, the bone securing element is a spiral thread or ridge (35, FIG. 3B) that extends along at least a portion of the external surface of the device. The thread can be a single continuous thread along all or a portion of the length of the device, or the thread can be interrupted in some portions (e.g., by cut-outs or openings in the wall of the core body of the device). Some devices can have more than one thread. In some instances, the pitch of the thread (407, FIG. 4) can be the same, and in some instances, the pitch of the thread may be variable. In these instances, the pitch of the thread (i.e., distance between the threads) may vary as desired. In some instances, the pitch ranges from 1 mm to 1 cm, such as 1.5 mm to 5 mm and including 2 mm to 3 mm. In some embodiments, the pitch may be variable along the length of the device, e.g., the pitch may be smaller at the distal end, and widen at the proximal end. In some embodiments, the pitch can be single or double start thread. The thread or ridge can in some instances have a sharp peak at the crest of the thread, as shown in FIG. 3B, 35 and can also be flattened at the crest of the thread, as shown in FIG. 3B, 32. The crest of the thread can be flattened over all or only a portion of the screw (e.g., the thread may be flattened at the proximal, or larger end of the screw). The flattening can result in an essentially planar configuration at the crest of the thread, with variable width (as shown in FIG. 4, element 403). The amount of flattening at the crest of the thread can be variable, e.g., the width of the crest can be equal to 5% of the height of the thread, 10%, 15%, etc.

The height of the thread (element 408, FIG. 4) can be the same along the length of the device, or it can vary.

For example, the thread height 408 can be greater at the distal end of the device than at the proximal end, or conversely greater at the proximal end of the device than at the distal end, such that a line drawn through the peaks of the crests form an angle (element 405, FIG. 4) that is not parallel to the line drawn along the core body of the device (element 404, FIG. 4).

The subject device can also have varying widths at the base of the threads (element 33, FIG. 3C, and element 409, FIG. 4), i.e., the distance between the distal face of one thread (element 401) and the proximal face of the adjacent thread (element 402). The device can also have various configurations of the base between the threads, e.g., the base between the threads can have a V-shape, or a U-shape, a convex or concave shape, a slope, etc. Additionally, as discussed above, the depth of the "valley" or conversely, the height of the thread or ridge can also vary along the length of the screw embodiment. For example, the grooves can be shallower at the proximal end in order to provide more surface for contact with the surrounding bone.

The angle formed by the slope of the distal face of one thread (element 401) and the proximal face of the adjacent thread (element 402) can vary, shown as element 406, FIG. 4. In some instances the angle is symmetric, i.e., the slope of 401 is the same as the slope of 402. In other instances the angle can be asymmetric, that is, the slope of 401 as measured from the base of the thread to the crest is different than the slope of 402 as measured from the base of the thread to the crest of the thread. The angle formed by adjacent threads can range from 0 (i.e., the slopes are parallel) to 170°, such as from 10 to 90°, or 15 to 60°.

The angle of the core body of the device, i.e., the angle formed between the distal point of the cone and the sides or walls of the cone (404) can vary, e.g., in some embodiments the cone can be wider, or have a larger angle, and in other embodiments the cone will be narrower, or have a smaller angle. Accordingly, the volume of the internal open space of the device embodiment will vary with changes in the above described angle. The volume of the internal open space will vary as well as with changes in length of the device, width of the internal passageway, etc.

The diameter may vary along the length of the device. In some instances, the diameter ranges from 3 mm to 3 cm, such as 5 mm to 2.5 cm, and including 5 mm to 2 cm. In some instances, the length of the device ranges from 3 mm to 6 cm, such as 4 mm to 5 cm and including 8 mm to 4 cm.

Alternative Wedge Implant Configurations

In addition to the trimodal embodiments described above, wedge implants finding use in certain embodiments of the methods include a number of alternative wedge implant configurations, e.g., as described in greater detail below.

Implants finding use in certain embodiments of the subject methods include those having a variety of different shapes, such as implants that have a generally conical, cylindrical, or oval shape. In some embodiments, one or both of the ends of the implant may be smooth and rounded. In some embodiments, one or both of the ends of the implant may be flat. In some embodiments, the implant may be tapered, such that the diameter of the implant varies along its length. Such tapering may include an increase, a decrease, or both an increase and a decrease in the diameter of the implant at various positions along the length of the implant.

In some embodiments, implants may include one or more threads. In some embodiments, a thread may originate at a first end of the implant and extend along the outer surface of the implant and terminate at the other end of the implant. In some embodiments, a thread may originate or terminate in a central portion of the implant, e.g., may originate or terminate at a position on the implant that is not an end of the implant. In some embodiments, an implant may have threads that do not cover the entire outer surface of the implant. For example, in some embodiments, an implant may have one or more areas or sections that are covered by a thread, and may also have one or more areas or sections that are not covered by a thread. Such unthreaded sections of an implant may extend along the entire length of the implant, or may only extend over a smaller portion of the implant. In some embodiments, an implant may have discontinuous threads such that the threads do not cover the entire surface of the implant, but instead leave a portion of the implant surface unthreaded.

In some embodiments, the threads of the implant may be flat. In some embodiments, the degree of flatness of the thread may change at various positions along the length of the thread. For example, in some embodiments, a thread may progressively soften over the length of the implant, such that the thread is flatter near a particular section of the implant.

In some embodiments, implants may include various openings at one or both ends of the implant or along the sides of the implant. In some embodiments, implants may be hollow or may have substantially hollow portions or segments. In some embodiments, implants may have a hollow central region such that an instrument may be inserted into and/or through the central region of the implant. In some embodiments, implants may be configured to change size, e.g., to expand, while in some embodiments, implants can be configured not to expand, e.g., to maintain the same size.

In some embodiments, implants may include surfaces that are generally smooth and flat that extend over a section of the implant. In some embodiments, implants may include surfaces with grooves, ridges, or surface treatments that extend over a section of the implant.

Examples of devices that may be used in the subject methods can include, but are not limited to, devices such those used for subtalar implants, vertebral implants, vertebral inter-body fusion devices, or interference screws used for Anterior Cruciate Ligament (ACL) fixation.

Figure 5B:
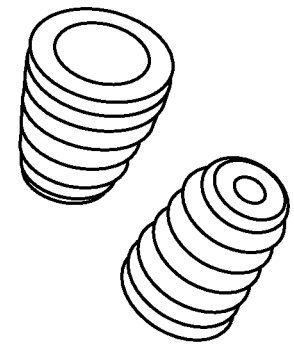
FIGS. 5A-5U provide illustrations of multiple different devices that can be used in methods of fracture reduction.
Figure 5A:
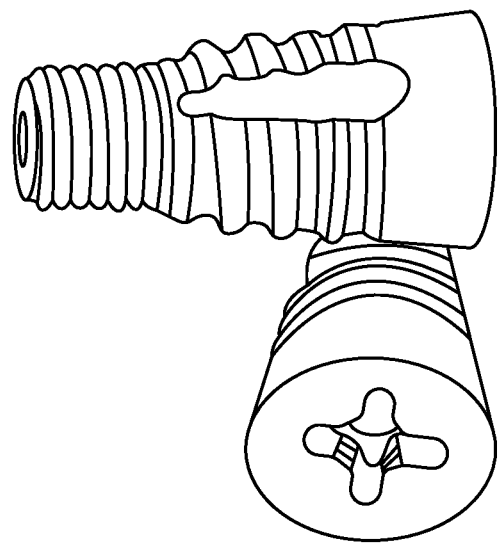
Figure 5D:
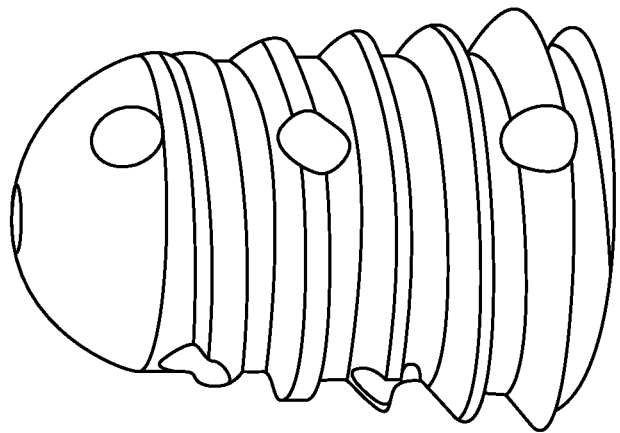
Figure 5C:
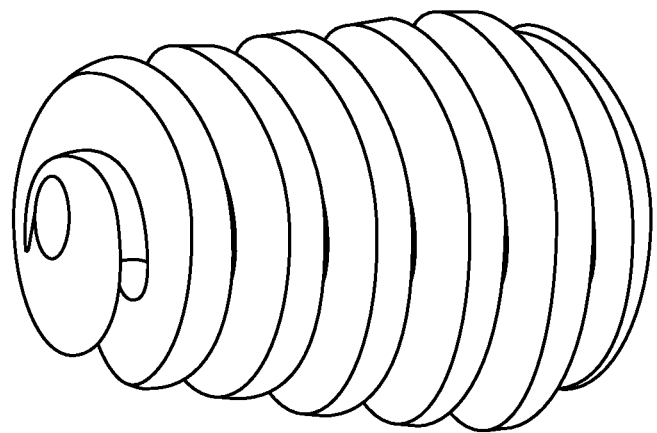
Figure 5E:
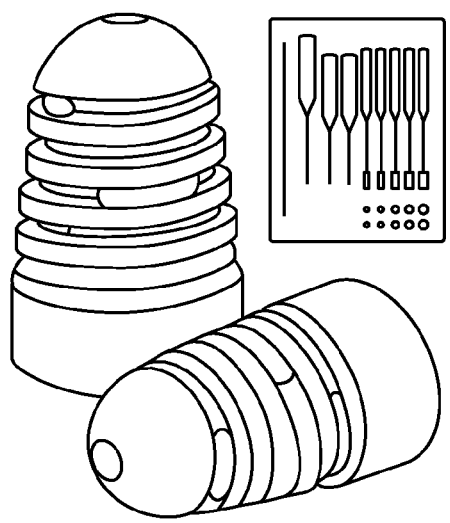
Figure 5F:
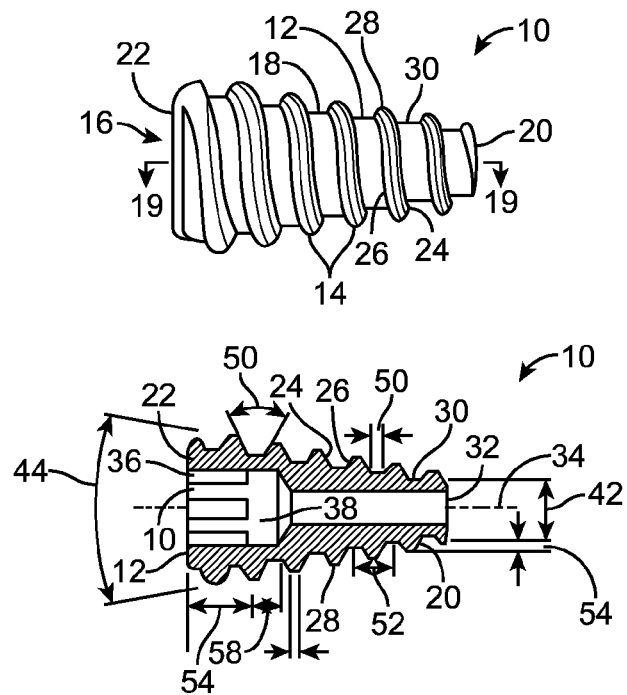
Figure 5G:
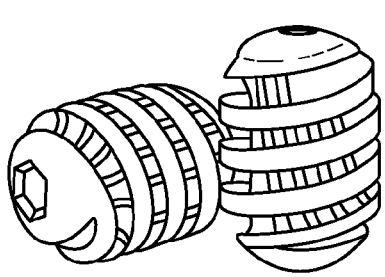
Figure 5H:
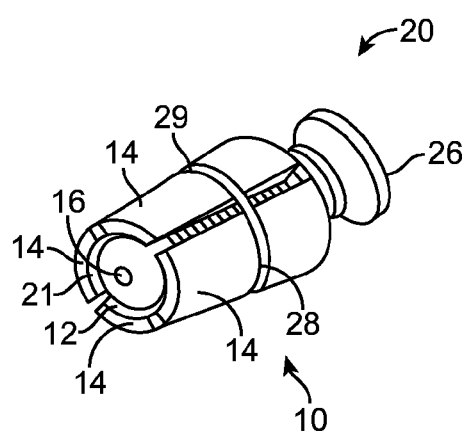
Figure 5Q:
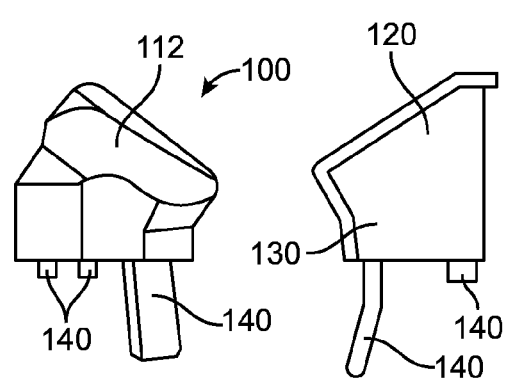
Figure 5R:
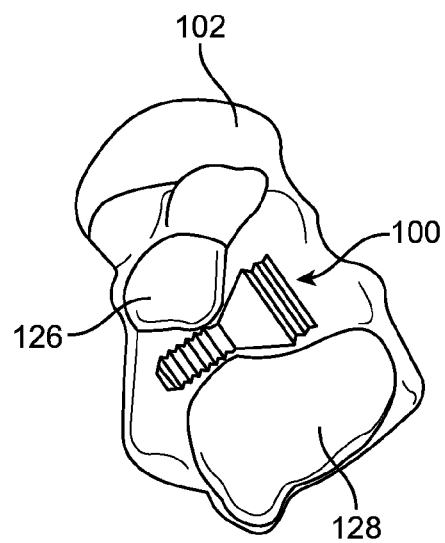
Figure 5S:
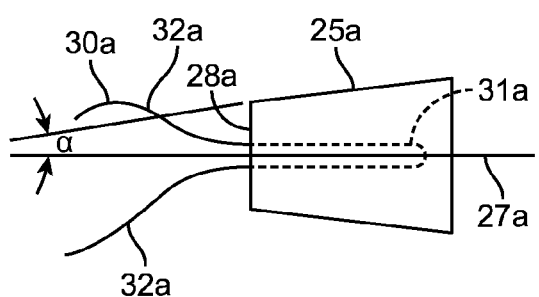
Figure 5T:
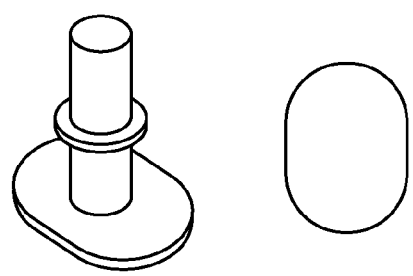
Figure 5U:
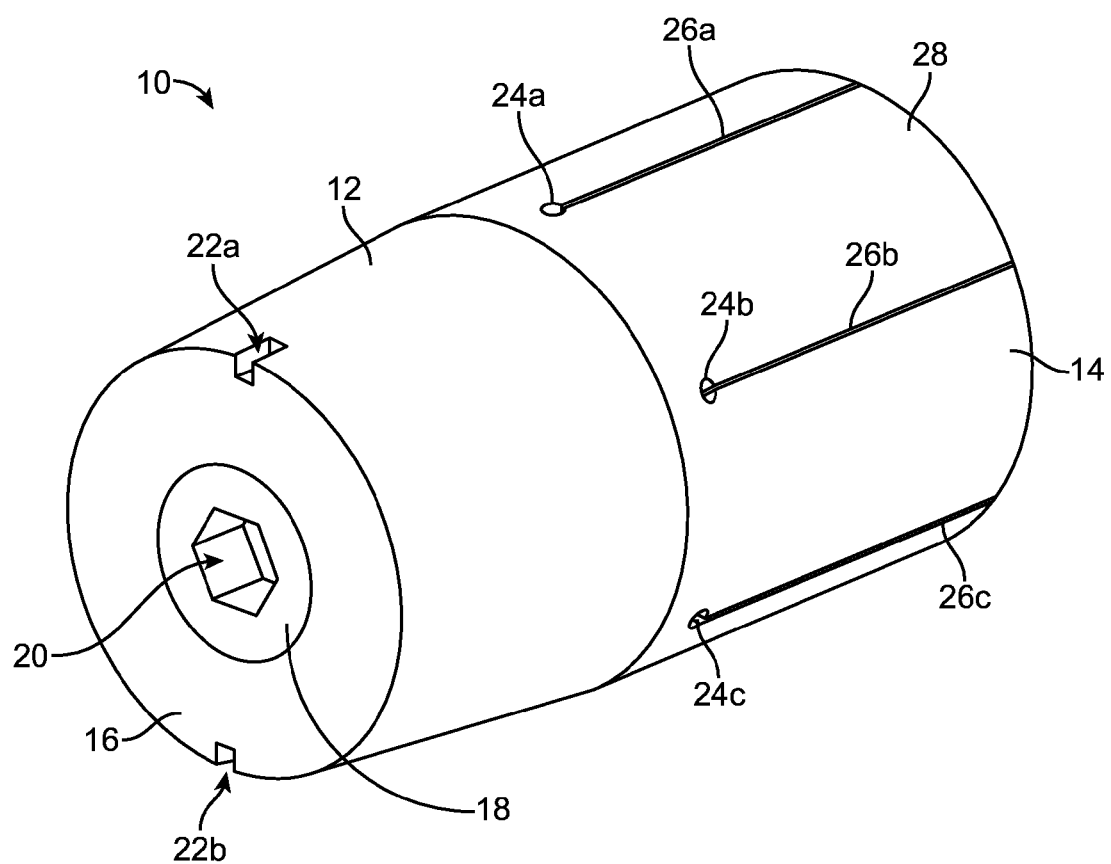

Examples of such implants are the Subfix™ Arthroeresis Implant made by Memometal, Inc. depicted in FIG. 5A, the Arthrex ProStop™ Arthroeresis Implant depicted in FIG. 5B, the Instratek Sub-Talar Lok™ Arthroeresis Implant System depicted in FIG. 5C, the Tornier Futura™ Conical Subtalar Implant depicted in FIG. 5D, the BioArch® device by Wright Medical depicted in FIG. 5E, the conical screw device by Osteomed depicted in FIG. 5F, the device depicted in FIG. 5G, a porous expansion bolt as described in U.S. Patent Publication No. 2011/0071579 depicted in FIG. 5H, the device by Integra Lifesciences, Corp. depicted in FIG. 5I, the device by Howmedica, Intl. depicted in FIG. 5J, the interbody fusion device by Warsaw Orthopedic, Inc. depicted in FIG. 5K, the subtalar implant by Biopro, Inc. depicted in FIG. 5L, the tapered bone screw by Accumed, LLC. depicted in FIG. 5M, the Talus of Vilex (TOW)) Subtalar implant device depicted in FIG. 5N, the implant by European Foot Platform depicted in FIG. 5O, the devices of the OrthoPro Conical Subtalar Spacer System depicted in FIG. 5P, the spacer device by Healthcare Creations, LLC depicted in FIG. 5Q, the sinus tarsi implant as disclosed in U.S. Pat. No. 7,033,398 depicted in FIG. 5R, the conical plug implant as disclosed in U.S. Pat. No. 4,450,591 depicted in FIG. 5S, the device as disclosed in design patent D274359 depicted in FIG. 5T, the expandable subtalar implant as disclosed in U.S. Patent Publication No. 2008/0208349 depicted in FIG. 5U, the conical screw by Mikai Orthopedic, an interference screw, e.g., as disclosed in Bach et al., Arthroscopy: The Journal of Arthroscopic and Related Surgery (2000) 16: 1-6; and U.S. Pat. Nos. 7,322,986; 6,875,216; 6,629,977; 6,045,554 and 5,456,685, etc.

In some embodiments, the devices are not "caged" devices, i.e., devices that include a first component present inside of a second cage component, such as those devices described in U.S. Patent Publication No. 2009/0182336.

Additional Optional Device Features

The subject devices can, in some embodiments, be configured to be delivered to a reduced bone fracture site of interest using one or more tools, such as a guidewire, extractor, a grasping tool, a screwdriver, etc. For example, in a cannulated or hollow conical screw embodiment, the device can be deployed to a fracture site using a guidewire. In another example, the device can be positioned in a fracture site by using a tool such as a screwdriver adapted for use with the device (e.g. a hex head, cruciate, Phillips, Torx, or other three-dimensional locking method).

The reduced bone fracture fixation devices described above can be made of a variety of biocompatible materials or metallic materials that combine strength and fatigue resistance. For example, the fixation device can be machined or formed using at least one of autograft or allograft bone, stainless steel, titanium, a nickel-titanium alloy such as nitinol, a nickel-cobalt alloy, another cobalt alloy, a vanadium alloy, tantalum, chromoly steel or CRMO, PEEK (polyaryletheretherketone), other biocompatible porous or non-porous metal alloys, allograft bone, polymers and plastics, and combinations or mixtures thereof. In some embodiments, the reduced bone fracture fixation devices or any portion thereof can include shape memory materials, which are materials that have a temperature induced phase change, e.g., a material that if deformed when cool, returns to its "undeformed", or original, shape when warmed.

In some embodiments, the fixation device may be coated with a substance, over the entire device or a portion of the surface of the device. In some embodiments, the coating can include a therapeutic agent (e.g., an antibiotic, an anti-inflammatory agent, or a bone morphogenic protein (BMP), an agent to promote osteo-integration (e.g., hydroxyapatite), a hardening agent (e.g., titanium nitride), an anodizing treatment, to provide various colors to different size devices, etc. In some embodiments, a fixation device may be coated with a combination of agents, e.g., antibiotics and anti-inflammatory agents; agents or features to promote osteo-integration, etc. In other embodiments, a fixation device may have more than one coating. For example, a reduced bone fracture fixation device can be coated with an antibiotic agent and also have an anodizing treatment applied to the device.

Methods

Aspects of the invention further include methods of treating a subject for a fracture, i.e., methods for repair of a bone fracture in a subject. Methods according to embodiments of the invention can include identifying a subject with a bone fracture, reducing the bone fracture, and then introducing into the reduced bone fracture a wedge implant comprising a body dimensioned to be positioned in the reduced bone fracture. The wedge implant device can be inserted into a bone or fracture void, such that body of the device is configured to exert a force on bone of the reduced bone fracture sufficient to maintain reduction of the bone or fracture void.

Methods of reducing a fracture can include a closed or open reduction, as is known to those of ordinary skill in the art (e.g., such as can be found in Campbell's Operative Orthopaedics, S. Terry Canale, Editor; or Operative Techniques in Orthopaedic Surgery, Sam Wiesel, Editor in Chief; Hand Surgery, Editors: Richard Berger & Arnold-Peter Weiss, Lippincott, Williams & Wilkins, 2004; Rockwood and Green's Fractures in Adults; or any suitable online resource such as Orthopaedic Knowledge Online (OKO), etc.)

Following reduction of a fracture, methods can include verification of the position and alignment of the fracture fragments, e.g., using an imaging method, such as an x-ray or portable intra-operative mini-fluoroscopy, etc.

Methods of introducing the subject devices into a reduced fracture site can include the selection of the correct size and/or configuration of the subject device. Selection of an appropriate device can be performed by medical personnel, e.g., a surgeon, prior to a procedure or during the procedure, and can include evaluation of imaging studies (e.g., x-ray, CT, MRI), measurements taken of the fracture site, measurements obtained of the fracture site in the operating or procedure room, etc.

Methods of the subject invention can also include the use of any suitable tools for assisting in the use of the device. Such tools may include, e.g., forceps, tweezers, clamps, graspers, applicators, screwdrivers adapted for use with the device (e.g. a form fit shape such as a hex, cruciate, Torx, or Phillips design), guidewires, sheaths, catheters, and any specially-designed tools.

The device may be implanted through an incision providing access to the bone or fracture void. For example, for a distal radial fracture, the incision may be volar-radial, i.e., the Henry approach, or dorsal-radial between the first and second dorsal compartments. The fracture may be approached around the first dorsal compartment, releasing the distal-most fibers of the brachioradialis if necessary, and accommodating the instrumentation for distraction and reduction. This procedure may be performed with manual reduction. Although the exemplary embodiments disclosed herein refer to implanting the device within a distal radial fracture, it is understood that the device may be implanted in other bone fractures, voids, or defects of other bones, e.g., vertebral bodies, calcaneous, etc. as discussed above.

For implantation of the device within a distal radial bone or fracture void, the distal end of the device may be inserted first so that it becomes positioned on an ulnar side of the fracture, or the device may be inserted in any other orientation. The device may also include bone securing elements. After implantation, the bone securing elements may attach to bone adjacent the bone or fracture void, thereby securing the device within the bone or fracture void. For example, the bone securing element may attach to bone on a distal side of the bone or fracture void, and the bone securing element may attach to bone on a proximal side of the bone or fracture void, or vice versa.

After implantation, the subject devices can maintain reduction of a fracture by acting as a cortical strut and a three-dimensional reduction device filling the metaphyseal void. The reduced bone fracture fixation device provides sufficient resistance to forces to maintain reduction of a fracture (e.g., compressive and torsional forces, which can pull the bone out of alignment during the fracture healing phase). In the case of a distal radius fracture, the healing process typically lasts from 4 to 8 weeks.

The reduced bone fracture fixation device can also provide load-sharing healing of the fracture site. Reduced and maintained fractures will heal even if some defect cavitation has occurred from the fracture itself, since the fracture has direct exposure to bone marrow elements with active bone cells (osteoblasts, osteoclasts, osteocytes, and other blood elements known to influence bone healing and remodeling) provided the fracture remains reasonably stable. Additionally, the subject devices do not require a second procedure for removal of the device, e.g., as required with conventional plate and screw fixation. However, these devices can be removed either in the acute setting due to unforeseen factors such as infection by direct manipulation and extraction. The devices can also be removed even in the setting of a healed fracture by unscrewing in the conical screw design, or controlled corticotomy with wireform compression, cutting, and removal. In the latter cases, the overall healed fracture integrity is maintain in a three-dimensional phase.

In some instances, methods of treating a reduced fracture can include using the subject devices with additional elements, including fixation elements, or synthetic bone graft, or any suitable bone cement. For example, a fracture of the proximal tibia may be successfully reduced and treated with a device of the subject invention (e.g., a device with a conical screw configuration) however there may be an additional bone fragment or fragments that can be positioned with a fixation device, such as a K-wire, plates, or pin. In another example, a fracture of the proximal humerus may be successfully reduced and treated with a device of the subject invention (e.g., a device with a cylindrical coil configuration), however the fracture void may be large enough to require "filler" in the form of bone graft including autograft or allograft, synthetic graft, or bone cements (e.g., calcium phosphate, calcium sulfate, etc.). In yet another example, a compression fracture of a vertebral body may be successfully reduced and treated with a device of the subject invention however the fracture void may be large enough to require "filler" in the form of e.g., a calcium phosphate cement.

After the reduced bone fracture has been treated, e.g., as described above, methods of treating the reduced fracture may include a period of immobilization, e.g., with a splint or cast. In some instances, the period of immobilization can range from one week to 3 months, such as from two weeks to 2 months, or 1 month to eight weeks. In embodiments in which an additional fixation device has been employed, the fixation device may need to be removed.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Manufacture of Devices

Methods of manufacturing the reduced bone fracture fixation device may include molding, stamping, wire forming or machining protocols, etc., as desired. Methods of manufacturing the reduced bone fracture fixation device may include applying one or more coatings to all or a portion of the device, as discussed above. Such coatings include but are not limited to therapeutic agents, osteo-integration agents, hardening agents, anodizing treatments, etc.

Kits

Also provided are kits that at least include the subject devices. The subject kits at least include a reduced bone fracture fixation device of the subject invention and instructions for how to use the device in a procedure. In some embodiments, the kits can include a set of two or more reduced bone fracture fixation devices. In other embodiments, a set of devices can include at least three reduced bone fracture fixation devices, e.g., four or more, five or more, six or more, etc.

In some embodiments, a set of reduced bone fracture fixation devices includes two or more devices in which at least two of the bone fracture fixation devices are of different sizes. For example, in one embodiment a set of three reduced bone fracture fixation devices can be provided in a "small" size; a "medium" size; and a "large" size, which can vary in length along the longest axis of the device. The set of reduced bone fracture fixation devices can also be provided as a set of devices configured for a particular fracture site; e.g. proximal tibia, proximal humerus, hip, etc. In other embodiments, a set of devices e.g., for the distal radius, can be provided with both different sizes, and different configurations, in which some configurations might be more suited for a particular fracture site than other configurations.

In some instances, devices of different size, or devices for different sites may be labeled in any suitable manner to distinguish one size from another, or to distinguish a device for one site from another. For example, a "small" size wrist fracture fixation device can have an anodized treatment imparting a red color to the device, while the "medium" size fracture fixation device can have an anodized treatment imparting a blue color to the device.

The kit can also include a sizing and/or measuring tool, which can be disposable, for determining a desired size or configuration of bone fracture fixation device by measuring one or more distances, such as the distance between the surfaces of reduced fracture, the extent of the fracture, etc. The measuring tool can be any suitable measuring device, such as a sizer, a template, a caliper, a sterile disposable flexible tape measure, etc.

The kit can also include one or more tools configured to position a reduced bone fracture fixation device in a reduced bone fracture. The positioning tools can be disposable. Such tools may include, e.g., forceps, tweezers, clamps, graspers, applicators, screwdrivers adapted for use with the device (e.g. a form fit tip using for example a hex, cruciate, Torx, or Phillips design), guidewires, sheaths, catheters, and any specially-designed tools.

Other elements which can be included in the kit include any suitable bone cement (e.g., calcium phosphate cement), synthetic bone graft, BMP, PMMA (polymethylmethacrylate) cement, etc., or, which can be used with subject devices at the fracture site. The kits can also include one or more separate fixation elements, such as a K-wire, plates, etc.

The instructions for using the devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g., CD-ROM, diskette, etc. The instructions may take any form, including complete instructions for how to use the device or as a website address with which instructions posted on the internet may be accessed.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A trimodal implant device comprising a body having a length extending between a proximal end and a distal point, being tapered along the length from the proximal end to the distal point, and defining a longitudinal axis, the body including:
    three faces extending along the length from the proximal end to the distal point;
    a plurality of cut-outs, each of the cut-outs extending through one of the three faces, each of the cut-outs further having a perimeter that tapers along the length between a proximal arcuate shape adjacent to the proximal end and a distal arcuate shape adjacent to the distal point, the proximal arcuate shape having a larger radius than the distal arcuate shape;
    a plurality of columnar elements separating each of the three faces from one another, each of the columnar elements having an exterior surface, having an interior surface opposite the exterior surface and opposing one of the cut-outs, and spanning from at least the proximal arcuate shape to the distal arcuate shape; and
    at least one thread originating at the distal point and spiraling around the body along the length thereof,
    wherein the tapering perimeter of each of the cut-outs extends through the respective face such that the respective cut-out terminates at an interior surface of the body,
    wherein the interior surface of at least a first columnar element of the plurality of the columnar elements includes adjacent walls defining a respective interior edge, and
    wherein a plane bisects the first columnar element and the respective cut-out opposing the interior surface of the first columnar element through the respective interior edge.

2. The device of claim 1, wherein the proximal end is open to a void space.

3. The device of claim 1, wherein the device includes a cross-sectional shape, at least at the proximal end, that is generally triangular.

4. The device of claim 1, wherein the thread extends from the distal point along at least a threaded portion of the exterior surface.

5. The device of claim 4, wherein the threaded portion extends to the proximal end, wherein a height of the thread at the distal point is greater than a height of the thread at the proximal end such that a line drawn through peaks of the thread along the length of the device is not parallel to a line drawn along the exterior surface of the device.

6. The device of claim 1, wherein the device is configured for use with a K-wire, plate or pin.

7. A fracture fixation kit comprising:
    the device of claim 1; and
    a K-wire, plate or pin.

8. The kit of claim 7, further comprising a set of instructions for how to use the device in a procedure.

9. A trimodal implant device comprising a body having a length extending between a proximal end and a distal point, the body including:
    an exterior surface that defines a first face, a second face and a third face tapering uniformly and continuously along the length from the proximal end to the distal point, each of the first, second and third faces being separated from one another by a rounded edge of a plurality of rounded edges, an external thread that originates at the distal point and continues along at least a threaded portion of the exterior surface; and an internal surface that is offset from the external surface by a thickness, the internal surface defining a hollow void space inside of the body that extends along a portion of the length between a distal-most portion adjacent to the distal point and a proximal-most portion adjacent to the proximal end, wherein the device includes a cross-sectional shape, at least at the proximal end, that is generally triangular, wherein each face has a cut-out offset from each rounded edge to define a proximal arcuate shape adjacent to the proximal end and a distal arcuate shape adjacent to the distal point, the proximal arcuate shape having a larger radius than the distal arcuate shape, wherein each cut-out is in communication with the hollow void space and opposes a respective interior surface of a respective rounded edge of the plurality of the rounded edges, wherein a cross-sectional shape of the hollow void space along a length of the body extending between a proximal end of the distal arcuate shape of the cut-out to a distal end of the cut-out differs from a cross-sectional shape of the hollow void space along a length of the body extending from the proximal end of the distal arcuate shape of the cut-out to a distal end of the proximal arcuate shape, wherein the interior surface of at least a first rounded edge of the plurality of the rounded edges includes adjacent walls defining a respective interior edge, wherein a plane bisects the interior surface of the first rounded edge and the respective cut-out opposing the interior surface of the first rounded edge through the respective interior edge, and wherein the thickness of the body is configured to sustain a separating force that is sufficient to maintain reduction of a reduced bone fracture.

10. The device of claim 9, wherein the proximal end of the body has an opening engageable with a positioning tool adapted to position the body in a reduced bone fracture.

11. The device of claim 10, wherein the opening is in communication with the hollow void space to define an internal passageway that extends through the proximal end of the body, and wherein the internal passageway is sized to receive the positioning tool.

12. The device of claim 9, wherein the device is configured for use with a K-wire, plate or pin.

13. A trimodal implant device comprising:

a body having a length between a proximal end and a distal point, the body comprising:

an exterior surface offset from an interior surface to define a shell with three generally triangular faces, each face being separated from the other faces by a respective rounded edge of a plurality of rounded edges and tapering uniformly and continuously along the length to the distal point so as to surround an internal void of the body;

an external thread that originates at the distal point and continues along a threaded portion of the body; and a plurality of spaced-apart cut-outs, each of the cut-outs opposing a respective interior surface of a respective rounded edge of the plurality of the rounded edges and having a tapering perimeter that extends through the shell at each of the three triangular faces, each of the cut-outs further interrupting the external thread of the threaded portion, being in communication with the internal void of the body, and defining a proximal arcuate shape adjacent to the proximal end and a distal arcuate shape adjacent to the distal point, wherein the distal point and each rounded edge are dimensioned to wedge the body into a reduced bone fracture, wherein the shell is configured to sustain a separating force that is sufficient to maintain reduction of the reduced bone fracture, wherein the tapering perimeter of each of the cut-outs extends through the shell such that the respective cut-out terminates at the interior surface of the body, wherein the interior surface of at least a first rounded edge of the plurality of the rounded edges includes adjacent walls defining a respective interior edge, and wherein a plane bisects the interior surface of the first rounded edge and the respective cut-out opposing the interior surface of the first rounded edge through the respective interior edge.

14. The device of claim 13, wherein the tapering perimeter of each cut-out tapers between a proximal semi-circle offset from the proximal end and a distal semi-circle offset from the distal point, the proximal semi-circle having a larger radius than the distal semi-circle.

15. The device of claim 14, wherein the external thread comprises a plurality of threads, each of the plurality of threads having a uniform lead.

16. The device of claim 15, wherein a pitch between at least two of the plurality of threads is different than the uniform lead.

17. The device of claim 14, wherein the threaded portion terminates at a central portion of the body.

18. The device of claim 14, wherein the body has a section comprising at least one non-threaded portion having at least one bone securing element selected from a group consisting of a groove, a ridge, a porous surface, and a combination thereof.

19. The device of claim 14, wherein a substance is applied to at least a section of the body, and wherein the substance is selected from a group consisting of an antibiotic, an anti-inflammatory agent, a bone morphogenic protein, an agent to promote osteo-integration, an anodizing treatment, and a combination thereof.

20. The device of claim 13, wherein the device is configured for use with a K-wire, a pin, or a plate.

* * * * *